United States Patent [19]

Shimizu et al.

[11] Patent Number: 4,810,794

[45] Date of Patent: Mar. 7, 1989

[54] PROCESS FOR PRODUCING PYRIDINE BASES

[75] Inventors: Shinkichi Shimizu, Hirakata; Nobuyuki Abe, Ikoma; Masanori Doba, Osaka; Akira Iguchi, Kyoto; Hiroshi Sato, Ibaraki; Ken-ichi Hirose, Settsu; Youichi Umada, Takatsuki, all of Japan

[73] Assignee: Koei Chemical Co., Ltd., Osaka, Japan

[21] Appl. No.: 9,526

[22] Filed: Feb. 2, 1987

[30] Foreign Application Priority Data

Feb. 6, 1986 [JP] Japan ................................. 61-24696
Nov. 29, 1986 [JP] Japan ............................... 61-285345

[51] Int. Cl.$^4$ ................. C07D 213/09; C07D 213/10; C07D 213/12
[52] U.S. Cl. ..................................... 546/251; 546/250
[58] Field of Search ............................... 546/250, 251

[56] References Cited

U.S. PATENT DOCUMENTS

| 3,970,655 | 7/1976 | Baylis ................................. 546/251 |
| 4,220,783 | 9/1980 | Chang et al. ....................... 546/251 |

FOREIGN PATENT DOCUMENTS

| 0131887 | 1/1985 | European Pat. Off. ............ 546/251 |
| 44-32790 | 4/1969 | Japan .................................. 546/251 |
| 46-41546 | 6/1971 | Japan .................................. 546/251 |
| 51-63176 | 10/1976 | Japan .................................. 546/251 |
| 60-38362 | 1/1985 | Japan .................................. 546/251 |

Primary Examiner—Alan L. Rotman
Attorney, Agent, or Firm—Stevens, Davis, Miller & Mosher

[57] ABSTRACT

Process for producing pyridine bases by reacting an aliphatic aldehyde and/or ketone with ammonia in gaseous phase in the presence of a catalyst, characterized by using a catalyst which is obtained by modifying a zeolite having an atomic ratio of Si to Al, Fe and/or Ga of 12 to 1,000 and a constraint index of about 0.8 to about 12 with at least one metal ion and/or metal compound selected from the group consisting of thallium, lead and cobalt.

20 Claims, No Drawings

PROCESS FOR PRODUCING PYRIDINE BASES

TECHNICAL FIELD

The present invention relates to a process for producing pyridine bases by reacting an aliphatic aldehyde and/or ketone with ammonia in gaseous phase using a specific zeolite catalyst, and particularly preferably, relates to a process for producing pyridine and picolines by reacting acetaldehyde and formaldehyde with ammonia in gaseous phase.

BACKGROUND OF THE INVENTION

Methods, by which pyridine bases are produced by reacting an aliphatic aldehyde and/or ketone with ammonia in gaseous phase using a solid acid catalyst such as amorphous aluminosilicate and the like, are known (Japanese patent application Kokai (Laid-Open) No. 63,176/76, Japanese Patent Publication Nos. 41,546/71, and 32,790/69).

It is known that crystalline aluminosilicate, so-called zeolite is used as the catalyst for producing pyridine bases from an aliphatic aldehyde and/or ketone and ammonia (U.S. Pat. No. 4,220,783 and Japnese patent application Kokai (Laid-Open) No. 38,362/85).

In the methods using amorphous aluminosilicate catalyst which are practiced industrially the yields, which are calculated based on the total number of carbon atoms of an aliphatic aldehyde and/or ketone, are as low as 50% at most and carbon is deposited on the catalyst due to side reactions, resulting in lowering of the activity within a short time. Therefore, it is necessary to reactivate the catalyst by periodical regeneration by aeration, and the repetition of reaction (deposition of carbon) and regeneration (overheat) brings deteriorations of catalytic activity and of mechanical strength of the catalyst.

Even when a zeolite is used as the catalyst, for example, U.S. Pat. No. 4,220,783 discloses that pyridine was obtained in such low yield as 40% by using an H form ZSM-5 or a ZSM-5 ion exchanged with cadmium, copper or nickel. Japanese patent application Kokai (Laid-Open) No. 38,362/85 discloses that acetaldehyde, formaldehyde and ammonia were used and in the case of fixed bed, the total "yield" of pyridine and β-picoline was 77%, the "yield" of pyridine which is more expensive than β-picoline economically being 51%. In the case of fluidized bed which is superior reaction system, the reaction was effected by using the same catalyst to obtain pyridine and picolines in a total "yield" of 88.8%, the yield of pyridine being 60.2%.

However, the yields are shown as the values calculated based on the amount of the acetaldehyde alone out of the amounts of acetaldehyde and formaldehyde (molar ratio of 1:1) used in the reaction, and if the yields are converted into the values calculated based on the total carbon number of acetaldehyde and formaldehyde, the total yield of pyridine and picolines is changed from 88.8% to 78.5% and the yield of pyridine is changed from 60.2% to 51.7%.

BRIEF SUMMARY OF THE INVENTION

An object of the present invention is to provide a process for synthesizing pyridine bases by using a specific zeolite catalyst.

DETAILED DESCRIPTION OF THE INVENTION

As a result of extensive research on the catalysts with which pyridine bases can be obtained with a higher efficiency, the present inventors have found that a high yield of pyridine can be obtained by using a zeolite having a high constraint index, which has been modified with at least one ion of and/or compound of metal selected from the group consisting of thallium, lead and cobalt, and achieved the present invention.

The present invention relates to a process for producing pyridine bases by reacting an aliphatic aldehyde and/or ketone with ammonia in gaseous phase in the presence of a catalyst, wherein the catalyst obtained by ion exchanging a zeolite having an atomic ratio of Si to Al, Fe and/or Ga of 12 to 1000 and a constraint index of about 0.8 to about 12, with thallium ion, lead ion and/or cobalt ion or the catalyst obtained by treating a zeolite having an atomic ratio of Si to Al, Fe and/or Ga is 12 to 1,000 and a constraint index of about 0.8 to about 12 with at least one metal compound selected from the group consisting of thallium compounds, lead compounds and cobalt compounds by a method of kneading, impregnation, immersion, deposition or evaporation to dryness is used.

The method of the present invention is described concretely.

The aliphatic aldehyde used in the present invention includes saturated aldehydes such as formaldehyde, acetaldehyde, propionaldehyde, butyraldehyde and the like as well as unsaturated aldehydes such as acrolein, methacrolein, crotonaldehyde and the like. Further, there may be used acetone, methyl ethyl ketone and the like as the aliphatic ketone.

The combination of aliphatic aldehydes and/or aliphatic ketones as the starting materials determines the main compounds of the pyridine bases to be produced. The typical examples are shown in the following Table 1.

TABLE 1

| Aldehyde, ketone | Main products formed |
| --- | --- |
| Acetaldehyde | α-Picoline, γ-picoline |
| Acetaldehyde + formaldehyde | Pyridine, β-picoline |
| Acrolein | β-Picoline |
| Acrolein + acetaldehyde | Pyridine |
| Acrolein + propionaldehyde | β-Picoline |
| Propionaldehyde + formaldehyde | 3,5-Lutidine |
| Crotonaldehyde + acetone | 2,4-Lutidine |
| Acetone + formaldehyde | 2,6-Lutidine |
| Acetone | 2,3,6-Collidine |

Among zeolites, those having an atomic ratio of Si to Al, Fe and/or Ga of 12 to 1,000, preferably 15 to 500, and a constraint index of about 0.8 to about 12 can be used as the starting materials for preparing the catalysts to be used in the present invention, which show a high catalytic performance.

The terms "constraint index" used herein is defined, for example, in an article written by Frillette et al. in Journal of Catalysis, 67, 218–222 (1981) and expresses the pore character of a catalyst. Although the value varies a little by a method of measurement, the results of measurement by Frillette et al. are shown in the following Table 2.

TABLE 2

| Zeolite and others | Constraint index |
| --- | --- |
| Amorphous silica alumina | 0.6 |
| REY | 0.4 |
| Mordenite (Y zeolon) | 0.4 |
| Silicalite S-115 | ~1 |
| ZSM-12 | 2 |
| Erionite | 3.8 |
| ZSM-35 | 4.5 |
| ZSM-5 | 8.3 |
| ZSM-11 | 8.7 |
| ZSM-23 | 9.3 |

The zeolites which can be used as the starting materials for preparing the catalysts to be used in the present invention are exemplified several zeolites including aluminosilicate such as ZSM-type zeolites, silicate S-115 and others, and heterosilicates such as Fe-silicate, Ga-silicate and others. Such zeolites are easily commercially available, and also are prepared by methods known in the art.

For example, zeolites of ZSM series are available from Mobil Catalysts Corp. of Japan. The methods for producing them are described in detail in U.S. Pat. Nos. 3,702,886 (ZSM-5), 3,709,979 (ZSM-11), 3,832,449 (ZSM-12), and 4,016,245 (ZSM-35). Furthermore, Fe- or Ga-silicate can easily be synthesized by method described in an article written by Inui, et al, [J. Synthetic Organic Chemistry, Japan, 44, 60–70 (1986)]. The silicalite S-115 which is available from Union Carbide Corp. and the preparation method is described in detail in U.S. Pat. No. 4,061,724.

The zeolite used in the present invention may be any of an alkali ion form such as sodium, postassium or the like, ammonium ion form and proton form. The alkali ion, however, is not preferably because it lowers the catalystic activity if it remains in the catalyst finally, and hence it is desirable to eliminate the alkali ion before, during or after modifying the zeolite with ion of and/or compound of metal selected from the group consisting of thallium, lead and/or cobalt. The zeolite to be subjected by ion-exchange treatment with thallium, lead and/or cobalt ions may be any one of alkali ion form, ammonium ion form or proton form, and the most preferable is ammonium form zeolite. Accordingly, it is desirable that a zeolite of an alkali ion form or proton form is previously ion exchanged into ammonium form by dipping it repeatedly several times in an aqueous solution of an ammonium salt such as ammonium chloride, ammonium nitrate, ammonium acetate or the like or in aqueous ammonia and filtering it.

Ion exchange into thallium ion, lead ion and/or cobalt ion is carried out by repeating procedures of dipping a zeolite having a constraint index of about 0.8 to about 12 of the above mentioned alkali ion form, ammonium form or proton form, preferably of ammonium ion form in an aqueous solution of chloride, nitrate, acetate or the like containing thallium ion, lead ion and/or cobalt ion with a concentration of 0.01 to 2 gram ion/l, ion exchanging it at a predetermined temperature with stirring and filtering it, and finally washing it with water. After the procedure, the ion-exchanged zeolite is usually dried at 100° to 200° C. and if desired, calcined to obtain a catalyst.

Further, modification of the zeolite with the above-mentioned metal compound by a method of kneading, impregnation, immersion, deposition or evaporation to dryness may be carried out by using H-form or $NH_4$-form zeolite, furthermore, by using zeolites previously ion-exchanged with at least one ion of metal selected from thallium, lead and cobalt may be used. The metal compound used in the present invention includes oxides, halides, sulfates, phosphates, nitrates, hydroxides, sulfides, silicates, titanates, borates, carbonates, organic carboxylates, organic chelates, and organometallic compounds. These compounds can be used either alone or in combination of two or more.

Specific examples are described below. (1) Powder of at least one metal compound selected from the group consisting of thallium compounds, lead compounds and cobalt compounds is kneaded with a zeolite as it is or together with water or the like and the resulting mixture is dried and then calcined. (2) A hydroxide obtained by neutralizing at least one metal compound such as nitrate, acetate or the like of a metal selected from the group consisting of thallium, lead and cobalt with aqueous ammonia solution or the like is kneaded with a zeolite and the resulting mixture is dried and calcined. (3) A zeolite is dispersed in an aqueous solution of at least one metal compound such as nitrate, acetate or the like of a metal selected from the group consisting of thallium, lead and cobalt, after which aqueous ammonia solution is added thereto, whereby the metal hydroxide is deposited on the surface of the zeolite, which is washed with water and dried and then calcined. (4) A zeolite is added to an aqueous solution of at least one metal compound selected from the group consisting of thallium compounds, lead compounds and cobalt compounds, and the resulting mixture is subjected to evaporation to dryness and then calcined.

Though the calcination is conducted usually in air or in a gas such as nitrogen, carbon dioxide or the like at 350° to 800° C. for several hours, the calcination is not always necessary because the catalyst is heated in a reactor.

The content of thallium, lead and/or cobalt in the zeolite which has been modified with the corresponding metallic ions and/or compounds is about 0.005 to 1.0 mg equivalent/g, though the preferable region varies depending on the kind of the zeolite and of the metal ion and compound.

The zeolite which has been ion exchanged with thallium ion, lead ion and/or cobalt ion or the zeolite which has been treated with at least one metal compound selected from thallium compounds, lead compounds and/or cobalt compounds by a method of kneading, impregnation, immersion, deposition or evaporation to dryness is molded as it is or after addition of silica, diatomaceous earth, kaolin, bentonite, alumina and/or aluminosilicate by means of a tablet machine into a columnar or cylindrical form, or it is kneaded with adding water, polyvinyl alcohol or vinylacetate and then molded by means of an extruder. Further, as a catalyst for fluidized bed, silica, diatomaceous earth, kaolin, bentonite, alumina and/or aluminosilicate is added together with water to the zeolite which has been ion exchanged with thallium ion, lead ion and/or cobalt ion or the zeolite which has been treated with at least one metal compound selected from thallium compounds, lead compounds and/or cobalt compounds by a method of kneading, impregnation, immersion, deposition or evaporation to dryness, to form a slurry, which is then subjected to spray drying, whereby spheral microbeads are formed. Also, a zeolite previously molded together with silica, diatomaceous earth, kaolin, bentonite, alumina and/or aluminosilicate may be modified with at least one metal ion selected from the group consisting of thallium, lead and/or cobalt ion by ion-exchanging, or with at least one metal compound selected from thallium compounds, lead compounds and/or cobalt compounds by a method of impregnation, immersion, deposition or evaporation to dryness. In either method, the molded product is calcined in the atmosphere or in a gas such as nitrogen, carbon dioxide or the like at 350° C. to 800° C. for several hours to impart a strength to the molded product and to eliminate volatile components which had been contained in the binder. However, because the catalyst is heated in a reactor, the calcination is not always necessary.

The reaction of the present invention may be conducted in a mode of fixed bed, fluidized bed or moving bed.

The molar ratio of ammonia to the aliphatic aldehyde and/or ketone is 0.5 to 5 mol/mol. The space velocity (SV) used is 100 to 10,000 $Hr^{-1}$, preferably 300 to 3,000 $Hr^{-1}$. The reaction temperature is preferably 350° C. to 600° C. Although the pressure of the reaction gases can be used in the range of from below the atmospheric pressure to several atmospheric pressures, usually the pressure in the range of from the atmospheric pressure to about 2 atmospheric pressures is used conveniently.

The particularly preferable combination of an aliphatic aldehyde or ketone for production of pyridine or $\beta$-picoline is a combination of acetaldehyde and formaldehyde, and the molar ratio of acetaldehyde: formaldehyde: ammonia is adjusted to 1:0.3-3: 0.5-5. In particular, when the catalyst of the present invention is used, pyridine which is more expensive than $\beta$-picoline is produced predominantly in the reaction products. As the combination of an aliphatic aldehyde or ketone for production of $\alpha$-picoline or $\gamma$-picoline, it is desirable to use acetaldehyde alone. The reaction can be effected without any trouble if the gaseous starting materials may contain water, methanol or the like. However, when acetaldehyde and formaldehyde are used as the starting materials, the amount of methanol is preferably up to 0.5 mole per mole of the acetaldehyde. Formaldehyde can be fed in a form of formalin. Further, as the aliphatic aldehyde or ketone, a dimer, a trimer, the other oligomers or polymers capable of generating a monomer of aliphatic aldehyde or ketone in an evaporator or a reactor can also be used.

Although deposition of carbon on the catalyst is detected during the reaction, the amount of the carbon deposited on the catalyst is smaller as the reasonable result of the higher yield of pyridine bases as compared with in conventional processes. Accordingly, the regeneration of the catalyst is easy. The regeneration of the catalyst is effected according to a conventional method, that is, a method which comprises burning out the carbon deposited on the catalyst by passing air through the catalyst layer at a temperature of 450° C. to 550° C.

By using the catalyst of the present invention, as shown, for example, in Example 1, the yield of pyridine and the total yield of pyridine and picolines become 63% and 81%, respectively, the yields being shown as the value calculated based on the total number of carbon atoms of the aldehyde and ketone as the starting materials, which means that economically more expensive pyridine can be obtained in a higher yield as compared with in conventional processes. Also, the amount of carbon deposited on the catalyst is small and the regeneration of the catalyst is easy.

The present invention is described below in more detail referring to Examples, to which the present invention is not limited.

The reaction results in Examples are calculated based on the total number of carbon atoms of the aliphatic aldehyde and ketone used as the starting materials, according to the following equations:

$$\text{Yield of pyridine (\%)} = \frac{\text{Total number of carbon atoms of produced pyridine}}{\text{Total number of carbon atoms of aldehyde and ketone as starting materials}} \times 100$$

$$\text{Yield of } \alpha, \beta, \gamma\text{-picolines (\%)} = \frac{\text{Total number of carbon atoms of produced } \alpha, \beta, \gamma\text{-picolines}}{\text{Total number of carbon atoms of aldehyde and ketone as starting materials}} \times 100$$

EXAMPLE 1

According to Yashima method [SHOKUBAI (catalysts), 23, (3), pp. 232, (1981)], zeolite ZSM-5 was synthesized as follows.

Solution A was prepared by mixing 433.4 g of distilled water, 4.6 g of aluminum sulfate, 55.8 g of tetra-n-propylammonium bromide and 40 g of sulfuric acid.

Solution B was prepared by mixing 320 g of distilled water and 453 g of sodium silicate No. 3.

Solution C was prepared by mixing 754 g of distilled water and 189 g of sodium chloride.

A stainless steel autoclave having 3 liters of volume was charged with the solution C. The solutions A and B were added thereto with vigorous stirring. The mixture was regulated so as to keep the pH at 9.5 to 11.

The autoclave was sealed and heated to 160° C. Hydrothermal synthesis was effected under this condition while continuing stirring for 20 hours. In this period, the inner pressure of the autoclave was 5 to 6 kg/cm$^2$.

After completion of the reaction, the reaction mixture was cooled to room temperature and the product was separated by filtration. After repetition of washing and filtration until the concentration of Cl$^-$ ion in the filtrate became 1 ppm or below, the product was dried at 110° C. for 16 hours and then calcined in air at 530° C. for 4 hours to obtain 112 g of white crystals of Na form ZSM-5. As a result of the measurement of X-ray diffraction, the crystals had a diffraction pattern coincident with that of ZSM-5 described in Japanese Patent Publication No. 10,064/71. The atomic ratio of Si/Al was found 90 as the result of analysis.

The Na form ZSM-5 was ion exchanged 3 times with 1 l each of 5% aqueous ammonium chloride solution at 50° C. to 60° C. for 1 hour and then filtered. After repetition of washing and filtration until the concentration of Cl$^-$ ion in the filtrate became 1 ppm or below, 106 g of crystals of NH$_4$ form ZSM-5 were obtained by drying at 110° C. for 16 hours.

With 40 ml of 0.1 M aqueous thallium nitrate solution was ion exchanged 4 g of the NH$_4$ form ZSM-5 at 80° C. for 2 hours and washed with 20 times larger amount of distilled water dividing into several times followed by drying at 110° C. for 16 hours and then calcining in air at 530° C. for 4 hours to obtain 3.5 g of Tl form ZSM-5 (Tl content: 3.0%).

A glass reaction tube having an inner diameter of 12.6 mm was filled with 3 g of this crystalline Tl form ZSM- 5. A mixture of 2 moles of acetaldehyde and 1 mole of formaldehyde (40% aqueous solution) was vaporized and mixed with 4 moles of preheated ammonia gas, and the resulting gaseous mixture was introduced at a SV of 1000 $Hr^{-1}$ into the reaction tube kept at 450° C. The reaction products were absorbed into water and then analyzed by a FID gas chromatography. Average yields of the products in a period of 3 hours from the start of the reaction were found 63% of pyridine, 6% of α-picoline, 9% of β-picoline and 3% of γ-picoline, the total yield being 81%.

EXAMPLES 2 and 3

Pb form ZSM-5 (Pb content: 1.6%) and a Co form ZSM-5 (Co content: 0.07%) were prepared by a method similar to that described in Example 1, except that lead nitrate and cobalt nitrate were substituted for the thallium nitrate, respectively.

The results of the same reactions as in Example 1 using these respectively as catalysts are shown in Table 3.

EXAMPLE 4

Na form ZSM-5 prepared by a method similar to that described in Example 1 was treated in 0.5N hydrochloric acid at 80° C., washed with water until Cl$^-$ ion was not detected in the washed water, and then dried at 120° C. for 10 hours, after which it was ion exchanged with thallium nitrate by a method similar to that described in Example 1 to prepare Tl form ZSM-5 (Tl content: 2.8%).

The result of the same reaction as in Example 1 using this as catalyst is shown in Table 3.

EXAMPLE 5

Pb form ZSM-5 (Pb content: 2.2%) having a Si/Al atomic ratio of 50 was prepared by a method similar to that described in Example 1, except that the the ratio of the starting materials was changed, and lead nitrate was substituted for the thallium nitrate.

The result of the same reaction as in Example 1 using this as catalyst is shown in Table 3.

EXAMPLE 6

Tl form ZSM-5 (Tl content: 3.3%) having a Si/Al atomic ratio of 18 was prepared by a method similar to that described in Example 1, except that the the ratio of the starting materials was changed.

The result of the same reaction as in Example 1 using this as catalyst is shown in Table 3.

EXAMPLES 7 to 9

Tl form silicalite (Tl content: 2.6%), Pb form silicalite (Pb content: 1.1%) and Co form silicalite (Co content: 0.07%) were prepared by changing a silicalite manufactured by Union Carbide Corp. which was substituted for the Na form ZSM-5, into NH$_4$ form and further ion-exchanging it with thallium nitrate, lead nitrate and cobalt nitrate by a method similar to that described in Example 1, resepctively.

The results of the same reactions as in Example 1 using these respectively as catalysts ar shown in Table 3.

EXAMPLES 10 to 12

Tl form silicalite molded material (alumina binder, Tl content: 3.2%), Tl form silicalite molded material (silica binder, Tl content: 3.0%) and Tl form silicalite molded material (Kaolin binder, Tl content: 3.4%) were prepared by treating a silicalite molded material (alumina binder) and silicalite molded material (silica binder) manufactured by Union Carbide Corp., and a silicalite obtained by kneading silicalite with kaolin as a binder (silicalite/kaoline=40/60), molding and calcining, by a method similar to that described in Example 1, respectively.

The results of the same reactions as in Example 1 using these respectively as catalysts are shown in Table 3.

EXAMPLE 13

The reaction was effected in the same manner as in Example 1 using the Pb form silicalite prepared in Example 8 as catalyst. The yields in a period of 20 minutes after 15 minutes passed from the start of the reaction were 63% of pyridine, 9% of α-picoline, 9% of β-picoline and 6% of γ-picoline, the total being 85%. The yields in a period of 20 minutes after 6 hours passed from the start of the reaction were 53% of pyridine, 6% of α-picoline, 10% of β-picoline and 4% of γ-picoline, the total being 71%.

EXAMPLE 14

A glass reaction tube having an inner diameter of 12.6 mm was filled with 3 g of the Pb form silicalite prepared in Example 8. One mole of acetaldehyde was vaporized and mixed with 1.5 moles of preheated ammonia gas, and the resulting gaseous mixture was introduced at a SV of 1000 $Hr^{-1}$ into the reaction tube kept at 450° C.

The reaction products were absorbed into water and then analysed by a FID gas chromatography. The yields were 2% of pyridine, 40% of α-picoline and 28% of γ-picoline, the total being 70%.

COMPARATIVE EXAMPLE 1

The NH$_4$ form ZSM-5 synthesized in Example 1 was calcined in air at 530° C. for 4 hours to prepare H form ZSM-5.

The result of the same reaction as in Example 1 was repeated by using this as catalyst and the result is shown in Table 4.

COMPARATIVE EXAMPLE 2

Cd form ZSM-5 (Cd content: 0.16%) was prepared by a method similar to that described in Example 1, except that cadmium nitrate was substituted for the thallium nitrate.

The result of the same reaction as in Example 1 using this as catalyst is shown in Table 4.

COMPARATIVE EXAMPLE 3

The same reaction as in Example 1 was effected by using Y type zeolite (TSZ-330HOA, manufactured by Toyo Soda Manufacturing Co., Ltd.) as catalyst and the result is shown in Table 4.

COMPARATIVE EXAMPLE 4

The same reaction as in Example 1 was effected by using silicalite manufactured by Union Carbide Corp. as catalyst and the result is shown in Table 4.

COMPARATIVE EXAMPLE 5

The same reaction as in Example 1 was effected by using aluminosilicate (N-631 L, manufactured by Nikki Kagaku Co., Ltd.) as catalyst and the result is shown in Table 4.

TABLE 3

| Example | Catalyst | Yield (%) Pyridine | α-Picoline | β-Picoline | γ-Picoline | Total |
|---|---|---|---|---|---|---|
| 1 | Tl form ZSM-5 (Si/Al = 90) | 63 | 6 | 9 | 3 | 81 |
| 2 | Pb form ZSM-5 (Si/Al = 90) | 60 | 7 | 8 | 4 | 79 |
| 3 | Co form ZSM-5 (Si/Al = 90) | 57 | 6 | 7 | 3 | 73 |
| 4 | Tl form ZSM-5 (Si/Al = 90) (ion exchanged with HCl) | 61 | 5 | 3 | 8 | 77 |
| 5 | Pb form ZSM-5 (Si/Al = 50) | 55 | 5 | 8 | 4 | 72 |
| 6 | Tl form ZSM-5 (Si/Al = 18) | 56 | 7 | 9 | 4 | 76 |
| 7 | Tl form silicalite | 61 | 6 | 8 | 3 | 78 |
| 8 | Pb form silicalite | 59 | 6 | 8 | 4 | 77 |
| 9 | Co form silicalite | 56 | 5 | 7 | 2 | 70 |
| 10 | Tl form silicalite molded material (alumina binder) | 61 | 5 | 6 | 3 | 75 |
| 11 | Tl form silicalite molded material (silica binder) | 58 | 5 | 8 | 5 | 76 |
| 12 | Tl form silicalite molded material (kaolin binder) | 61 | 5 | 6 | 3 | 75 |

TABLE 4

| | Catalyst | Yield (%) Pyridine | α-Picoline | β-Picoline | γ-Picoline | Total |
|---|---|---|---|---|---|---|
| Comparative Example 1 | H form ZSM-5 | 42 | 3 | 11 | 5 | 61 |
| 2 | Cd form ZSM-5 | 43 | 4 | 9 | 4 | 60 |
| 3 | Y type zeolite | 27 | 5 | 14 | 8 | 54 |
| 4 | Silicalite | 41 | 3 | 12 | 5 | 61 |
| 5 | Aluminosilicate (N-631L by Nikki) | 33 | 4 | 11 | 4 | 52 |

EXAMPLES 15 and 16

According to the description of Japanese patent application Kokai (Laid-Open) No. 52,699/79 (Example 5), zeolite ZSM-11 was synthesized under the following conditions: Sodium silicate was used as a supplying source of silica, aluminum sulfate was used as a supplying source of alumina, and heptylenediamine was used as a template. Crystallization was effected at 160° C. for 10 days with stirring. The composition of the reaction mixture was as follows: $SiO_2/Al_2O_3=90$, $H_2O/SiO_2=40$, $Na/SiO_2=0.59$ and diamine/$SiO_2=0.02$. The product was washed, dried, and calcined in air by a conventional method, after which it was confirmed by measurement of X-ray diffraction to be ZSM-11. The resulting Na form ZSM-11 was further changed into each of Tl form ZSM-11 (Tl content: 3.2%) and Pb form ZSM-11 (Pb content: 1.8%) through $NH_4$ form in the same manner as in Examples 1 and 2, respectively.

The same reactions as in Example 1 were effected by using these respectively as catalysts. The average yields in a period between 5 hours passed and 10 hours passed from the start of the reaction are shown in Table 5.

TABLE 5

| | | Yield (%) | Picoline | | | |
|---|---|---|---|---|---|---|
| Example | Catalyst | Pyridine | α | β | γ | Total |
| 15 | Tl form ZSM-11 | 60 | 5 | 8 | 5 | 78 |
| 16 | Pb form ZSM-11 | 57 | 5 | 9 | 5 | 76 |

EXAMPLE 17

For 4 hours was further calcined 106 g of dry crystals of $NH_4$ form ZSM-5 obtained by a method similar to that described in Example 1 in air at 530° C. to obtain 95 g of H-form ZSM-5.

Aqueous ammonia solution was added to 20 ml of aqueous solution containing 0.15 g of thallium (I) nitrate to neutralize it, and the resulting precipitate was washed with water to obtain pasty thallium hydroxide. The pasty thallium hydroxide and 4 g of the H form ZSM-5 mentioned above were kneaded uniformly in a mortar, then dried at 110° C. for 14 hours and calcined in air at 530° C. for 4 hours to prepare H form ZSM-5/$Tl_2O$ ($Tl_2O$ content: 2.8%).

The result of same reaction as in Example 1 was effected by using this as catalyst, shown in Table 6.

EXAMPLES 18 and 19

H form ZSM-5/PbO (PbO content: 2.8%) and H form ZSM-5/CoO (CoO content: 0.30%) were prepared by a method similar to that described in Example 17, except that lead nitrate and cobalt nitrate were substituted for the thallium nitrate, respectively.

The results of the same reactions as in Example 1 using these respectively as catalysts, are shown in Table 6.

EXAMPLE 20

H form ZSM-5/PbO (PbO content: 3%) was prepared by mixing uniformly 4 g of the H form ZSM-5 prepared by a method similar to that described in Example 17 and 0.12 g of lead oxide in a mortar and then calcining the resulting mixture at 530° C. for 4 hours.

The result of the same reaction as in Example 1 using this as catalyst shown in Table 6.

EXAMPLE 21

$NH_4$ form ZSM-5 having a Si/Al ratio of 18 was passed by a method similar to that described in Example 6. The $NH_4$ form ZSM-5 modified with 0.20 g of thallium (I) nitrate through H form ZSM-5 by a method similar to that described in Example 17 to prepare H form ZSM-5/ $Tl_2O$ ($Tl_2O$ content: 3.8%).

The result of the same reaction as in Example 1 using this as catalyst, is shown in Table 6.

EXAMPLE 22

NH$_4$ form ZSM-5 having a Si/Al atomic ratio of 50 was prepared by a method similar to that described in Example 5. The NH$_4$ form ZSM-5 was modified with 0.04 g of cobalt (II) nitrate through H form ZSM-5 by a method similar to that described in Example 17 to prepare H form ZSM-5/CoO (CoO content: 0.25%).

The result of the same reaction as in Example 1 using this as catalyst, is shown in Table 6.

EXAMPLES 23 to 25

Silicalite (S-115) manufactured by Union Carbide Corp. was modified with each of thallium (I) nitrate, lead nitrate and cobalt nitrate by a method similar to that described in Example 17, whereby each of S-115/Tl$_2$O (Tl$_2$O content: 2.9%), S-115/PbO (PbO content: 2.2%) and S-115/CoO (CoO content: 0.10%) was prepared.

The results of the same reactions as in Example 1 using these respectively as catalysts, are shown in Table 6.

EXAMPLES 26 and 27

A silicalite molded material (alumina binder)/ Tl$_2$O (Tl$_2$O content: 3.0%) and a silicalite molded material (silica binder)/Tl$_2$O (Tl$_2$O content: 3.0%) were prepared by adding 4 g of a silicalite molded material (alumina binder) manufactured by Union Carbide Corp., and silicalite molded material (silica binder), which were respectively, to 10 ml of aqueous solution containing 0.15 g of thallium (I) nitrate, which were then evaporated to dryness with stirring, after which the residues were dried at 120° C. for 8 hours and then calcined a 530° C. for 4 hours.

The results of the same reaction as in Example 1 using these respectively as catalyst, are shown in Table 6.

EXAMPLE 28

A small amount of water was added to 4 g of an H form ZSM-5/Tl$_2$O prepared by a method similar to that described in Example 17 and 1 g of kaolin, which were kneaded and molded, and calcined at 530° C. for 4 hours to prepare a molded material of H form ZSM-5/Tl$_2$O (kaolin binder).

The result of the same reaction as in Example 1 using this as catalyst, is shown in Table 6.

EXAMPLE 29

The reaction was effected under the same conditions as in Example 1 using the S-115/PbO (PbO content: 2.2%) prepared, by a method similar to that described in Example 24 as catalyst. The average yields in a period of 20 minutes after 15 minutes passed from the start of the reaction were 64% of pyridine, 6% of α-picoline, 7% of β-picoline and 4% of γ-picoline, the total being 81%. The average yields in a period of 20 minutes after 6 hours passed from the start of the reaction were 56% of pyridine, 6% of α-picoline, 9% of β-picoline and 4% of γ-picoline, the total being 75%.

EXAMPLE 30

A glass reaction tube having an inner diameter of 12.6 mm was filled with the S-115/PbO (PbO content: 2.2%) prepared by a method similar to that described in Example 24. One mole of acetaldehyde was vaporized and mixed with 2 moles of preheated ammonia gas, and the resulting gaseous mixture was introduced at a SV of 1000 Hr$^{-1}$ into the reaction tube kept at 450° C. The reaction products were absorbed into water and then analysed by a FID gas chromatography. The average yields in a period of 3 hours from the start of the reaction were 2% of pyridine, 40% of α-picoline and 28% of γ-picoline, the total being 70%.

TABLE 6

| Example | Catalyst | Pyridine | Picoline α | β | γ | Total |
|---|---|---|---|---|---|---|
| 17 | ZSM-5/Tl$_2$O (Si/Al = 90) | 63 | 6 | 8 | 4 | 81 |
| 18 | ZSM-5/PbO (Si/Al = 90) | 61 | 6 | 8 | 4 | 79 |
| 19 | ZSM-5/CoO (Si/Al = 90) | 56 | 6 | 8 | 3 | 73 |
| 20 | ZSM-5/PbO (Si/Al = 90), kneading with PbO | 60 | 5 | 8 | 4 | 77 |
| 21 | ZSM-5/Tl$_2$O (Si/Al = 18) | 57 | 6 | 8 | 5 | 76 |
| 22 | ZSM-5/CoO (Si/Al = 50) | 55 | 5 | 9 | 4 | 73 |
| 23 | S-115/Tl$_2$O | 62 | 6 | 8 | 4 | 80 |
| 24 | S-115/PbO | 60 | 6 | 8 | 4 | 78 |
| 25 | S-115/CoO | 55 | 6 | 7 | 3 | 71 |
| 26 | S-115/Tl$_2$O (alumina binder molded material) | 60 | 6 | 6 | 4 | 76 |
| 27 | S-115/Tl$_2$O (silica binder molded material) | 58 | 6 | 8 | 4 | 76 |
| 28 | S-115/Tl$_2$O (kaolin binder molded material) | 60 | 5 | 8 | 3 | 76 |

EXAMPLES 31 and 32

The NH$_4$ form ZSM-11 obtained in Example 15 was changed into each of H form ZSM-11/Tl$_2$O (Tl$_2$O content: 3.2%) and H form ZSM-11/PbO (PbO content: 1.8%) through H form method similar to that described in Examples 17 and 18 respectively.

The same reactions as in Example 1 were effected by using these respectively as catalysts. The average yields in a period between 5 hours passed and 10 hours passed from the start of the reaction are shown in Table 7.

TABLE 7

| Example | Catalyst | Pyridine | Picoline α | β | γ | Total |
|---|---|---|---|---|---|---|
| 31 | ZSM-11/Tl$_2$O | 60 | 6 | 8 | 4 | 78 |
| 32 | ZSM-11/PbO | 58 | 5 | 8 | 4 | 75 |

EXAMPLE 33

Crystalline iron silicate zeolite was synthesized by a method as follows.

Solution A was prepared by mixing 34 g of Fe(NO$_3$)$_3$.9H$_2$O, 34 g of tetra-n-butylammonium chloride and 150 g of distilled water.

Solution B was prepared by suspending 70 g of fumed silica in 700 g of distilled water to obtain a suspension.

Solution C was prepared by dissolving 7.4 g of sodium hydroxide in 50 g of distilled water.

Into the solution C, there were mixed with solutions A and B, then thus obtained mixture was heated at 160° C. for 60 hours in an autoclave with stirring. The pH of the reaction mixture was changed from 12.4 to 11.4. A solid matter thus obtained was washed with water, so as to become the pH of the washed water to 7.3. There was obtained 72.7 g of white solid product. This product was determined as having the crystalline structure of zeolite ZSM-5 by X-ray diffraction analysis.

Thus obtained Na form iron silicate zeolite was subjected to ion-exchange treatment three times with 1 liter of 5% aqueous ammonium chloride solution at 50°–60° C. for 1 hour. Then the ion-exchanged zeolite was washed with water so as to the concentration of Cl$^-$ ion in the washed water become lower than 1 ppm. NH$_4$ form ion silicate zeolite was obtained by drying at 110° C. for 16 hours. A part of the zeolite was further calcined at 530° C. for 4 hours in air to obtain H form iron silicate zeolite.

Next, 20 ml of an aqueous solution containing 0.15 g of thallium (I) nitrate was neutralized by adding a certain amount of aqueous ammonia, and the precipitates obtained in the solution was collected by filtration and washed with water to obtain thallium hydroxide in paste form. Said thallium hydroxide was kneaded uniformly with 4 g of H form iron silicate zeolite in a mortar, and dried at 110° C. for 14 hours, further calcined in air at 530° C. for 4 hours to prepare H form iron silicate/Tl$_2$O (Tl$_2$O content: 2.8%).

The result of the same reaction as in Example 1 using this as catalyst is shown in Table 8.

EXAMPLE 34

4 Grams of NH$_4$ form iron silicate zeolite prepared in Example 33 was subjected to ion-exchange treatment with 40 ml of an aqueous solution containing 0.1 M-lead nitrate at 80° C. for 2 hours, then the ionexchanged zeolite was washed with distilled water in an amount of 20 times the quantity of the zeolite, by dividing the amount of water into several portions and washed in several times. The washed zeolite was dried at 110° C. for 16 hours, then further calcined in air at 530° C. for 4 hours to prepare Pb form iron silicate (Pb content: 1.5%).

The result of the same reaction as in Example 1 by using this as catalyst is shown in Table 8.

EXAMPLE 35

By a method similar to that described in Example 33, except that by using 4.87 g of Ga(NO$_3$)$_3$.9H$_2$O in place of Fe(NO$_3$)$_3$.9H$_2$O, there was synthesized Na form gallium silicate zeolite having the crystal structure of zeolite ZSM-5. After subjected the thus obtained Na form gallium silicate zeolite by ion-exchange treatment to convert it into NH$_4$-form gallium silicate zeolite, the resulting zeolite was further converted into Co form gallium silicate zeolite (Co content: 0.08%) by a method similar to that described in Example 34, except that by using cobalt nitrate in place of lead nitrate.

The results of the same reaction as in Example 1, using this zeolite as catalyst is shown in Table 8.

EXAMPLE 36

By a method similar to that described in Example 35, except that by using thallium nitrate in place of cobalt nitrate, there was prepared Tl form gallium silicate zeolite (Tl content: 2.9%).

The result of the same reaction conducted as in Example 1, using this zeolite as catalyst is shown in Table 8.

TABLE 8

| Ex- | | Yield (%) | | | | |
|---|---|---|---|---|---|---|
| am- | | | | Picoline | | |
| ple | Catalyst | Pyridine | α | β | γ | Total |
| 33 | H form iron silicate/Tl$_2$O | 55 | 6 | 12 | 6 | 79 |
| 34 | Pb form iron silicate | 56 | 7 | 12 | 7 | 82 |
| 35 | Co form gallium silicate | 54 | 5 | 11 | 5 | 75 |
| 36 | Tl form gallium silicate | 56 | 8 | 13 | 6 | 83 |

What is claimed is:

1. A process for producing pyridine bases by reacting an aliphatic aldehyde of the formula R$^1$CHO wherein R$^1$ is hydrogen or alkyl having 1 to 3 carbon atoms or alkenyl having 2 to 3 carbon atoms and/or a ketone of the formula R$^2$COR$^3$ wherein R$^2$ is methyl or ethyl and R$^3$ is methyl with ammonia in a gaseous phase, the mole ratio of ammonia to aliphatic aldehyde and/or ketone being 0.5 to 5.0 and the reaction temperature being between 350° to 600° C., in the presence of a catalyst obtained by modifying a zeolite having an atomic ratio of Si to Al, Fe and/or Ga of 12 to 1,000 and a constraint index of about 0.8 to about 12 with at least one ion of and/or at least one compound of a metal selected from the group consisting of thallium, lead and cobalt.

2. A process according to claim 1, wherein acetaldehyde and formaldehyde are used as the aliphatic aldehyde and the main product is pyridine.

3. A process according to claim 2, wherein the molar ratio of acetaldehyde: formaldehyde: ammonia is 1:0.3–3:0.5–5.

4. A process according to claim 2, wherein methanol is added to the starting materials in an amount of up to 0.5 mole per mole of acetaldehyde.

5. A process according to claim 1, 2 or 3, wherein the zeolite has been ion exchanged with a metal ion of metal selected from the group consisting of thallium, lead and cobalt.

6. A process according to claim 1, 2 or 3, wherein the zeolite is treated with at least one compound of a metal selected from the group consisting of thallium, lead and cobalt by a method of kneading, impregnation, immersion, deposition or evaporation to dryness.

7. A process according to claim 6, wherein the metal compound of thallium, lead and/or cobalt is at least one metal compound selected from the group consisting of oxides, halides, sulfates and phosphates of the same.

8. A process according to claim 7, wherein the metal compound of thallium, lead and/or cobalt is oxides of the same.

9. A process according to claim 7, wherein the modification method with the metal compound of thallium, lead and/or cobalt comprises kneading the zeolite with oxide or hydroxide of the same.

10. A process according to claim 6, wherein the content of the metal compound of thallium, lead and/or cobalt is 0.005 to 0.1 mg equivalent per g of the zeolite.

11. A process according to claim 5, wherein the content of the metal ion of thallium, lead and/or cobalt is 0.005 to 0.1 mg equivalent per g of the zeolite.

12. A process according to claim 1, wherein acetaldehyde is used as the aliphatic aldehyde and the main products comprise α-picoline and γ-picoline.

13. A process according to claim 1, wherein acrolein is used as the aliphatic aldehyde and the main products comprise β-picoline and pyridine.

14. A process according to claim 1, wherein formaldehyde is used as the aliphatic aldehyde, acetone is used as the aliphatic ketone and the main product comprises 2,6-lutidine.

15. A process according to claim 1, 2, 3, 12, 13 or 14, wherein the proportion of Si to the metals comprising Al, Fe, and/or Ga in the zeolite is about 15 to 500.

16. A process according to claim 1, 2, 3, 12, 13 or 14, wherein the zeolite is ZSM-5.

17. A process according to claim 1, 2, 3, 12, 13 or 14, wherein the zeolite is ZSM-11.

18. A process according to claim 1, 2, 3, 12, 13 or 14, wherein the zeolite is a gallium silicate having a crystal structure of ZSM-5 or ZSM-11 type.

19. A process according to claim 1, 2, 3, 12, 13 or 14, wherein the zeolite is an iron silicate having a crystal structure of ZSM-5 or ZSM-11 type.

20. A process according to claim 1, 2, 3, 12, 13 or 14, wherein the catalyst contains silica, diatomaceous earth, kaolin, bentonite, alumina and/or silica alumina.

* * * * *